United States Patent
Kulcinski et al.

(10) Patent No.: US 7,367,984 B2
(45) Date of Patent: May 6, 2008

(54) METHODS AND APPARATUS FOR SIZING FRESH DONOR HEART VALVES

(75) Inventors: David L. Kulcinski, Orange, CA (US); Luis A. Salazar, Chino Hills, CA (US); Dana K. Swanson, Murrieta, CA (US); Gary T. Tsuruta, Lake Forest, CA (US); Roxanna K. Kendall, Riverside, CA (US)

(73) Assignee: Medtronic, Inc., Minneapolis, MN (US)

( * ) Notice: Subject to any disclaimer, the term of this patent is extended or adjusted under 35 U.S.C. 154(b) by 663 days.

(21) Appl. No.: 10/434,372

(22) Filed: May 7, 2003

(65) Prior Publication Data

US 2004/0225320 A1 Nov. 11, 2004

(51) Int. Cl.
*A61M 29/00* (2006.01)
*A61B 5/107* (2006.01)

(52) U.S. Cl. ............... 606/198; 606/191; 600/587; 128/897

(58) Field of Classification Search ............. 33/512, 33/555, 511, 783, 784, 813, 819, 827, 6, 797, 33/707, 800, 792, 794–796, 810, 824, 542, 33/544.3; 623/1.24, 1.26, 2.1, 2.11; 600/587, 600/547; 606/191–198; 128/897, 898
See application file for complete search history.

(56) References Cited

U.S. PATENT DOCUMENTS

| | | | | |
|---|---|---|---|---|
| 2,785,471 A | * | 3/1957 | Aldeborgh et al. ............ | 33/800 |
| 2,828,546 A | * | 4/1958 | Campbell ..................... | 33/560 |
| 2,938,272 A | * | 5/1960 | Conklin ....................... | 33/501.2 |
| 3,225,447 A | * | 12/1965 | Bryant ......................... | 33/792 |
| 3,537,184 A | * | 11/1970 | Hearn ......................... | 33/199 R |
| 3,997,923 A | | 12/1976 | Possis ........................... | 3/1.5 |
| 4,372,743 A | | 2/1983 | Lane ........................... | 8/94.11 |
| 4,680,031 A | | 7/1987 | Alonso ......................... | 623/2 |
| 4,685,474 A | * | 8/1987 | Kurz et al. .................. | 600/591 |
| 4,726,121 A | * | 2/1988 | Ray et al. .................... | 33/806 |
| 4,892,541 A | | 1/1990 | Alonso ......................... | 623/2 |
| 4,935,030 A | | 6/1990 | Alonso ......................... | 623/2 |
| 5,032,128 A | | 7/1991 | Alonso ......................... | 623/2 |
| 5,197,979 A | | 3/1993 | Quintero et al. .............. | 623/2 |
| 5,327,908 A | * | 7/1994 | Gerry ........................... | 600/587 |
| 5,454,175 A | * | 10/1995 | Li ................................ | 33/797 |
| 5,562,729 A | | 10/1996 | Purdy et al. ................... | 623/2 |
| 5,800,438 A | * | 9/1998 | Tuke et al. ................... | 606/90 |
| 5,885,228 A | * | 3/1999 | Rosenman et al. ......... | 600/587 |
| 6,001,126 A | | 12/1999 | Nguyen-Thien-Nhon ...... | 623/2 |
| 6,110,200 A | * | 8/2000 | Hinnenkamp .............. | 623/2.11 |

(Continued)

*Primary Examiner*—Glenn K. Dawson
*Assistant Examiner*—Kathleen Sonnett
(74) *Attorney, Agent, or Firm*—Mike Jaro; Jeffrey J. Hohenshell (57) ABSTRACT

A fresh donor tissue valve isolation annulus size comprising a handle and trigger or crank knob manipulated by the user moves a movable probe into proximity with a stationary probe so that the probes can be inserted into the tissue valve lumen. The user releases the trigger or crank, and a biasing mechanism urges the movable probe away from the stationary probe until the resistance presented by the valve annulus equals the biasing force. A gage coupled to the movable probe displays a measure of the valve annulus diameter as a function of the distance that the movable probe moves away from the stationary probe until restrained from further movement by the fresh tissue valve annulus.

28 Claims, 9 Drawing Sheets

U.S. PATENT DOCUMENTS

| | | |
|---|---|---|
| 6,139,575 A | 10/2000 | Shu et al. .................. 623/2.12 |
| 6,176,877 B1 | 1/2001 | Buchanan et al. ......... 623/2.39 |
| 6,217,611 B1 | 4/2001 | Klostermeyer ............. 623/2.38 |
| 6,458,155 B1 * | 10/2002 | Van Nguyen et al. ..... 623/2.11 |

* cited by examiner

METHODS AND APPARATUS FOR SIZING FRESH DONOR HEART VALVES

FIELD OF THE INVENTION

This invention relates to methods of manufacturing bioprosthetic heart valves for human implantation to replace a defective heart valve from donor heart valves harvested from an animal and, more particularly, to a sizer and method of sizing fresh donor heart valves to facilitate the selection of donor heart valves to be fabricated into bioprosthetic heart valves.

BACKGROUND OF THE INVENTION

Implantable heart valve prostheses have been used to replace various diseased or damaged native or natural aortic valves, mitral (bicuspic) valves, pulmonic valves and tricuspid valves of the heart. Prosthetic heart valves can be used to replace any of these naturally occurring valves, although repair or replacement of the aortic or mitral valves is most common because they reside in the left heart chambers responsible for maintaining cardiac output of oxygenated blood. The aortic and mitral valves are most frequently replaced due to heart disease, congenital defects or injury. The mitral valve controls the flow of blood between the left atrium and the left ventricle and the aortic valve controls the blood flow from the left ventricle into the aorta. Generally, the known heart valve prostheses are either bioprostheses or mechanical heart valve prostheses.

Modern mechanical heart valve prostheses are typically formed of an annular valve seat in a relatively rigid valve body and one or more occluding disk or pair of leaflets that is movable between a closed, seated position in the annular valve seat and an open position in a prescribed range of motion. Such mechanical heart valves are formed of blood compatible, non-thrombogenic materials, typically currently comprising pyrolytic carbon and titanium. Hinge mechanisms and/or pivoting guides entrap and prescribe the range of motion of the disk or leaflets between open and closed positions. Exemplary bi-leaflet mechanical heart valves are disclosed in commonly assigned U.S. Pat. Nos. 4,935,030 and 6,139,575 and in U.S. Pat. Nos. 6,176,877 and 6,217,611.

The bioprostheses or "tissue valves" or "xenografts" (hereafter "tissue valves") are generally made of suitable donor heart valves harvested from an animal and treated with a preservative and fabricated as described further herein. The most widely used tissue valves include some form of stationary metal or plastic frame or synthetic support, referred to as a "stent", although so-called "stentless" tissue valves are available. The most common tissue valves are constructed using an intact, multi-leaflet, harvested donor tissue valve, or using separate leaflets cut from bovine (cow) pericardium, for example. The most common intact donor tissue valve used for stented and stentless valves is the porcine (pig) aortic valve, although valves from other animals (e.g., equine or marsupial donors) have been used. The present invention is not limited to the preparation of porcine valves, though existing tissue valves on the market are nearly exclusively made from porcine valves, and thus the description herein will focus on such tissue valves.

Exemplary tissue valves formed of swine valve leaflets mounted to struts of a stent are those disclosed in U.S. Pat. Nos. 4,680,031, 4,892,541, and 5,032,128 as well as the MEDTRONIC® Hancock II® and Mosaic® stented tissue valves. Some prosthetic tissue valves are formed from treated integral swine valve leaflets and valve annulus structure, e.g., the MEDTRONIC® Freestyle® stentless aortic root bioprostheses.

Mechanical and tissue valves have advantages and disadvantages. By their very nature, mechanical heart valves have metal or plastic surfaces exposed to the blood flow, which remain thrombogenic even long time after their implantation by major surgery. The opening and closing of mechanical heart valve occluders can damage blood elements and trigger a coagulant cascade. Blood flow disturbances in certain mechanical valves are also believed to aggravate blood coagulation. Therefore, patients having such mechanical heart valves can avoid potentially life threatening embolus formation only by taking anti-thrombogenic or anti-coagulant medication on a regular basis. Porcine tissue valves include three cusps or leaflets of a heart valve excised from pigs and preserved by treatment with glutaraldehyde. The preserved porcine tissue is thrombogenic, and therefore, the human patient takes anti-thrombogenic or anti-coagulant medication at least a period of time after the surgical implantation of a tissue valve. Valve leaflet opening and closing characteristics and blood flow past open tissue leaflets of tissue valves can be superior to those afforded by mechanical valves. However, tissue leaflets can become calcified over time distorting the leaflet shape and ultimately leading to failure of the tissue leaflets to fully close or open. Proposals have been advanced to form mechanical heart valve prostheses from flexible, anti-thrombogenic, polymeric sheets or fabrics that are resistant to calcification mounted to stents to function like stented tissue valves also been proposed as exemplified by U.S. Pat. No. 5,562,729. However, calcification and tear issues of polymeric materials remain to be solved before a polymeric valve can be realized.

Such mechanical valves and tissue valves are intended to be sutured to peripheral tissue of a natural heart valve orifice (the "valvar rim") after surgical removal of damaged or diseased natural valve structure from the patient's heart. Modern prosthetic heart valves are typically supplied with a sewing or suturing ring surrounding the valve body or stent that is to be sutured by the surgeon to the valvar rim. Suturing rings typically comprise a fabric strip made of synthetic fiber that is biologically inert and does not deteriorate over time in the body, such as polytetrafluoroethylene (e.g., "Teflon PTFE") or polyester (e.g., "Dacron"), that is woven having interstices permeable to tissue ingrowth. The valve body or stent is typically circular or ring shaped having an outer surface or sidewall shaped to fit with an inner sidewall of the suturing ring. In some cases, the suturing ring fabric is shaped to extend outward to provide a flattened collar or skirt that can be applied against and sutured to the valvar rim, as shown for example in U.S. Pat. No. 3,997,923.

To assure a proper fit, the patient's tissue annulus must be "sized" to indicate the size of the mechanical valve or tissue valve to be implanted in the valvar rim. In particular, proper fit of the annular valve body within the tissue annulus of the excised native valve is required. Typically, a set of sizers is supplied by the prosthetic heart valve manufacturer corresponding to the different sizes of available prosthetic heart valves. The surgeon inserts the sizers through the prepared annulus defined by the valvar rim to determine which corresponding prosthetic heart valve will best fit the valvar rim. The surgeon usually must attempt to size the annulus several times with one or more sizers of different diameters until the best fit is recognized.

Conventional sizers for measuring the human valve annulus typically comprise a series of incrementally sized cylindrical elements marked with the corresponding outside diameter in mm. Most sizer sets include cylindrical elements that range from a low of 19 mm to a high of 33 mm, in 2 mm increments, and a common handle for manipulating the sizers. Some sizers for measuring the human valve annulus are shaped, or include flanges or other stepped features to also provide a measurement of the aortic root adjacent to the annulus. The aortic root is that part of the valve anatomy between the annulus and the convex sinuses of the ascending aorta, and has a generally scalloped appearance with the valve leaflets being attached along alternating arcuate cusps and upstanding commissures around its border. In any event, the primary measurement derived from conventional surgical sizers is the annulus diameter determined by finding which sizer fits properly in the annulus based on tactile feedback.

A different approach to sizing the prepared valvar rim annulus is set forth in U.S. Pat. No. 6,110,200. The '200 patent discloses a single sizing apparatus that can be adjusted through a range of diameters to measure an anatomical tissue annulus. The apparatus includes an elongated support member having a proximal end and a distal end. An operator actuated movable member is joined to the proximal end of the elongated support member while an adjustable member is joined to the distal end of the elongated support member. The adjustable member has a reference axis and an outer curved surface selectively positionable in response to the operator actuated member. In particular, the outer curved surface can be selectively positioned between an inner position proximate the reference axis and an outer position spaced apart from the reference axis.

In one embodiment, a fluid passageway extends from the proximal end to the distal end an elongated support member, and an operator actuated movable member is joined to the proximal end of the elongated support member for providing fluid through the passageway to the distal end. An expandable, balloon-like member mounted to the distal end of the elongated support member receives the fluid. The expandable member having a reference axis and a substantially continuous outer curved surface disposed about the reference axis and selectively positionable in response to fluid provided by the operator actuated movable member between an inner position proximate the reference axis and an outer position spaced apart from the reference axis.

Preferably, an indicator is mounted to the elongated support member for determining a dimension of the outer curved surface. The indicator includes indicia representative of selected radial distances of the outer curved surface from the reference axis. A detent mechanism rotates with the shaft and selectively engages releasable stop surfaces on the indicator. The stop surfaces correspond to the various indicia on the indicator. The stop surfaces hold the shaft in each of the selected angular positions, which in turn, maintains the outer curved surface at each selected radial distance from the reference axis.

Thus, it is necessary to manufacture and distribute prosthetic heart valves in a variety of sizes to fit the sized annulus of a prepared valvar rim. The tissue valve manufacturer must have a supply of fresh donor heart valves from animals from which the range of tissue valves are fabricated. A typical prosthetic valve fabrication process for manufacturing porcine tissue valves in a variety of sizes is described in U.S. Pat. No. 6,458,155, for example.

As set forth in the '155 patent, fresh porcine hearts are first harvested in a certified slaughterhouse, weighed, and sorted into various valve size ranges by either estimating the annulus by eye, based on the flattened aortic width, or by estimating valve orifice size from heart weight. Of course, this correlation is a very rough estimate, with actual valve annulus sizes differing quite a bit within similarly sized porcine hearts. The aortic valve and surrounding tissue including a section of the pulmonary artery (hereinafter termed the "aortic valve isolation") is then severed from the porcine heart.

A batch of aortic valve isolations are packed in ice and shipped from the slaughterhouse to the prosthetic valve manufacturing facility. At the manufacturing facility, the aortic valve isolation is further sorted by valve size by technicians trained to estimate such valve size using their fingers. That is, the orifice diameter of the aortic valve annulus is estimated by insertion of one or more fingers through the inflow end of the aortic valve isolation. Because of the rough nature of the heart weight to valve size estimation, a large proportion of valves are rejected at this stage, resulting in wasted inventory and shipping costs.

The accepted aortic valve isolations are then trimmed and chemically fixed to render the donor tissue valves biologically inert for implantation in human patients. The trimming procedure typically involves cutting away the pulmonary artery and surrounding muscle tissue from the inflow end of the aortic valve isolation. The remaining donor tissue valve is generally tubular having a small amount of tissue on the inflow side of the annulus and the internal leaflets enclosed and protected by the tubular ascending aorta.

Chemical fixation may be accomplished using a variety of techniques and chemicals, though the most common procedure used involves supporting the tubular tissue valve element on at least the ascending aorta or outflow portion with a fixation insert, immersing the assembly in a bath of fixing solution (e.g., glutaraldehyde), and either flowing fixing solution through the tissue valve element or maintaining a predetermined pressure differential across the leaflets during the fixation process. See, for example, U.S. Pat. No. 4,372,743, which describes maintaining a low pressure differential across the leaflets of between 1-4 mm Hg.

The use of fixation inserts is also quite effective in shaping the tissue valve during the fixation process. For example, U.S. Pat. No. 5,197,979 describes inserts having three outwardly convex regions for shaping the tissue valve sinuses. More recently, U.S. Pat. No. 6,001,126 discloses inserts having a plurality of pinholes in the two convex regions corresponding to the coronary sinuses that enable coronary artery shaping plugs or mandrels to be mounted thereon. Whichever type of insert is used, the ultimate size of the fixed tissue valve is influenced, at least in the sinus regions, by the insert. Preferably, the relative size of the annulus and sinus regions is identical to the human aortic tissue valve being replaced. It is therefore very important to begin with a donor tissue valve having an accurately sized annulus.

The fixation process causes some shrinkage in the donor tissue valve. Therefore, the sizing of the annulus of the fresh donor tissue valve provides only an estimate of the annulus size of the fixed tissue valve. The amount of shrinkage depends on the chemicals used, the duration of fixation, the pressure differentials maintained within the tissue valve annulus during fixing, the temperature during fixing, and other less significant factors. Because of these variables, the annulus of fixed porcine aortic tissue valves are sized once again using a caliper and/or a sizing stent to sort the tissue valves into mounting sizes.

It is thus apparent that an accurate and reliable means for estimating, from the fresh donor tissue valve, the annulus size of a fixed xenograft tissue valve annulus is needed to increase tissue valve yield and quality, and reduce expense.

The above-referenced '155 patent discloses an apparatus for sizing fresh donor heart tissue valves that have a lumen and an inwardly directed tissue valve annulus within the lumen. The apparatus includes a sizing member having an axially extending, preferably conical, sizing portion with a forward end adapted to insert within the lumen of the donor heart tissue valve. The sizing portion increases in size along an axis from the forward end such that a region on the exterior thereof eventually contacts the tissue valve annulus upon continued insertion of the sizing portion within the lumen. A measuring bracket connects to the sizing member and has a scale portion spaced from and generally aligned with the sizing portion, the scale portion providing markings indicating the annulus size of the donor heart tissue valve relative to the position of the donor heart tissue valve on the sizing portion. The measuring bracket may include a mounting portion generally perpendicular to the scale portion and including a through hole into which the sizing portion fits. The markings are desirably supplemented with numerical indicators of tissue valve size, either in terms of tissue valve diameter in millimeters or as non-dimensional numbers in conjunction with a separate chart to correlate the numerical indicators with tissue valve size. The markings may be calibrated for fresh donor tissue valves from a particular geographic supply source.

The method of use of the sizing member disclosed in the above-referenced '155 patent includes inserting the forward end of the sizing portion into the donor heart tissue valve lumen, and halting the insertion at a predetermined resistance to further insertion. After halting further insertion of the sizing portion into the lumen, the tissue valve annulus size is determined based on the distance that the sizing portion has been inserted. In a preferred embodiment, the sizer further includes a measuring bracket connected thereto having a scale portion spaced from and generally aligned with the sizing portion. The tissue valve size is determined by observing the position of the donor heart tissue valve with respect to the scale portion of the measuring bracket.

A number of problems can arise in using the sizing member of the '155 patent. The user must select the tissue valve isolation and insert the tip of the conical sizing member into the valve lumen, pushed the tissue valve isolation over the conical surface as far as the valve annulus will go, to read the indicia on the surface, and to then pull the tissue valve isolation back off the conical sizing member. In doing so, care must be taken to avoid stretching the tissue valve annulus unduly. It is necessary for the user to keep the conical surface clean so that the conical sizing member can be easily inserted into the tissue valve lumen to the correct extent and then be easily removed from the tissue valve lumen. The estimation of the tissue valve lumen size is somewhat subjective for these reasons and because the tissue valve isolation covers the indicia on the conical surface at the tissue valve lumen.

It would also be difficult to use the conical probe within the lumens of harvested donor tissue valve isolations that include a long, curved aortic root as is used in preparation of certain tissue valve prostheses.

BRIEF SUMMARY OF THE INVENTION

The present invention provides an improved method and valve annulus sizer for sizing a fresh donor heart tissue valve isolation, comprising a fresh tissue valve having a lumen and an inwardly-directed annulus, that is simple to use and provides an accurate measurement of the annulus size. The annulus size is close to the valve lumen diameter but the annulus size is measured across the folded down tissue valve leaflets. For convenience herein, the measurement of annulus size and the measurement of the valve lumen diameter are used interchangeably herein.

The present invention involves inserting a pair of probes into the tissue valve lumen, separating the probes apart within the lumen into contact with the tissue valve annulus until the probes are restrained from further movement by the tissue valve annulus, and measuring the distance that the probes are moved apart, whereby the measurement provides an indication the valve lumen diameter for sizing the tissue valve annulus.

In preferred embodiments, the fresh donor tissue valve isolation annulus sizer comprises a handle assembly and a trigger assembly or crank assembly manipulated by the user to move a movable probe into proximity with a stationary probe so that the probes can be inserted into the tissue valve lumen. The user releases the trigger or crank, and a biasing mechanism urges the movable probe away from the stationary probe until the resistance presented by the valve annulus equals the biasing force. A gage coupled to the movable probe displays a measure of the valve annulus diameter as a function of the distance that the movable probe moves away from the stationary probe until restrained from further movement by the fresh tissue valve annulus. The gage reading is preferably resettable to a reference value display, e.g., all zeros, when the trigger is employed draw the movable probe to the starting position.

In one preferred embodiment, the handle grip and trigger are arranged as a pistol grip, and the trigger is grasped by one or more finger to draw the trigger away from the frame and toward the handle to move the movable probe to the starting position. In a second preferred embodiment, the trigger comprises a crank knob that is engaged by the thumb and depressed downward alongside the frame to move the movable probe to the starting position.

Advantageously, the user can release the trigger in a controlled manner to control the rate of movement of the movable probe and the elongation of the valve annulus to avoid undue stretching of the valve annulus tissue and to provide an accurate reading of the valve lumen diameter.

The sizer of the present of the invention facilitates the manufacturing of prosthetic heart tissue valves. A supply of fresh donor heart tissue valve isolations is provided at a slaughterhouse. The annulus size of the heart tissue valve isolations is measured using a sizer of the present invention having sizing probes for insertion within the lumen of the tissue valve isolation. The method includes selecting a subset of the supply of tissue valve isolations based on the step of measuring, and shipping the subset from the slaughterhouse to a tissue valve manufacturing facility. Finally, at least one tissue valve prosthesis is fabricated from a donor heart tissue valve isolation selected from the subset.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE INVENTION

In the following detailed description, references are made to illustrative embodiments of methods and apparatus for carrying out the invention. It is understood that other embodiments can be utilized without departing from the scope of the invention. Preferred methods and apparatus are described for accessing the pericardial space between the epicardium and the pericardium as an example of accessing an anatomic space between an outer tissue layer and an inner tissue layer.

Figure 1:
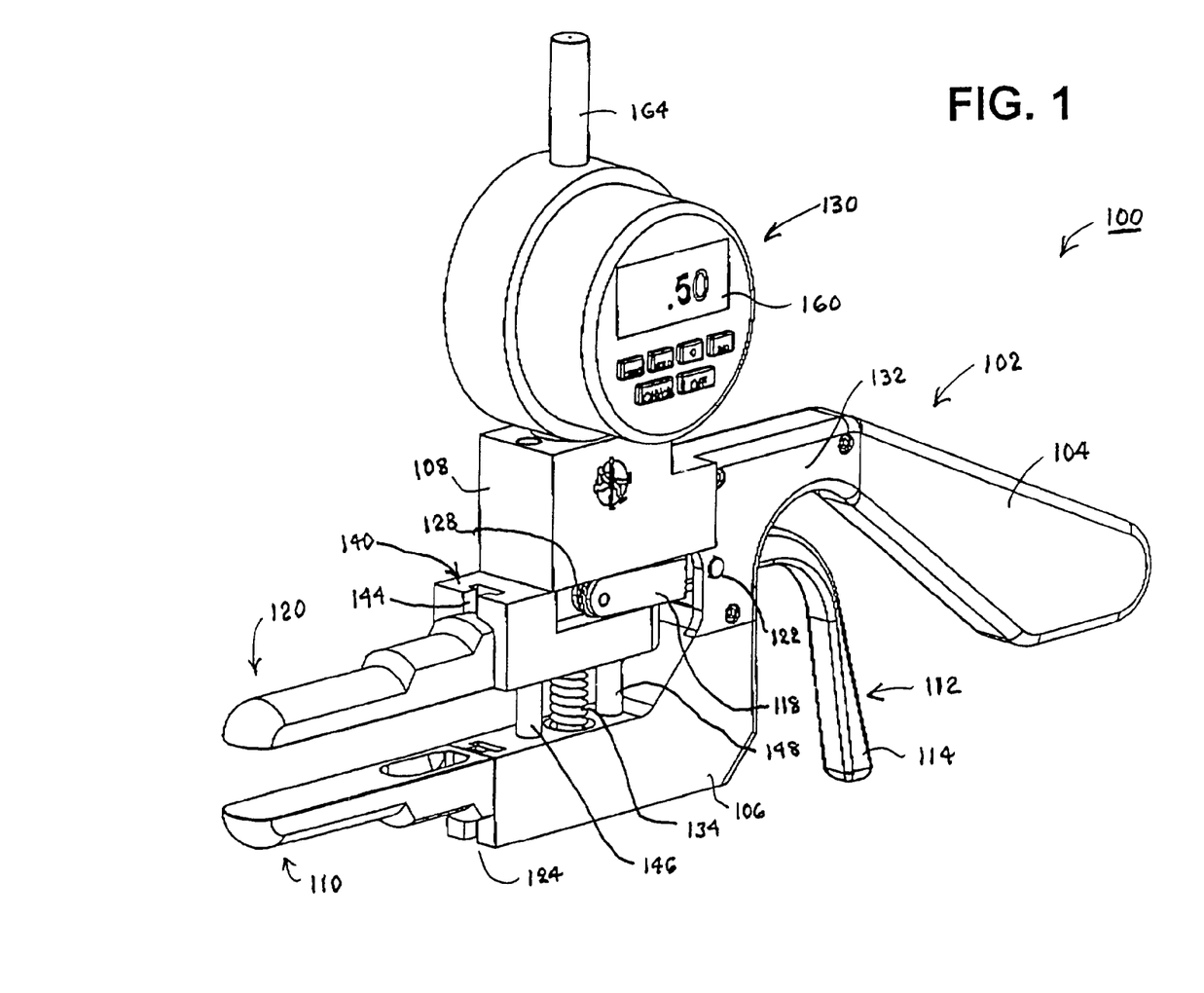
FIG. 1 is a perspective view of a first embodiment of a valve lumen sizer of the present invention with the fixed and movable probes in a measuring position upon release of the trigger in accordance with the first embodiment of the invention.
Figure 2:
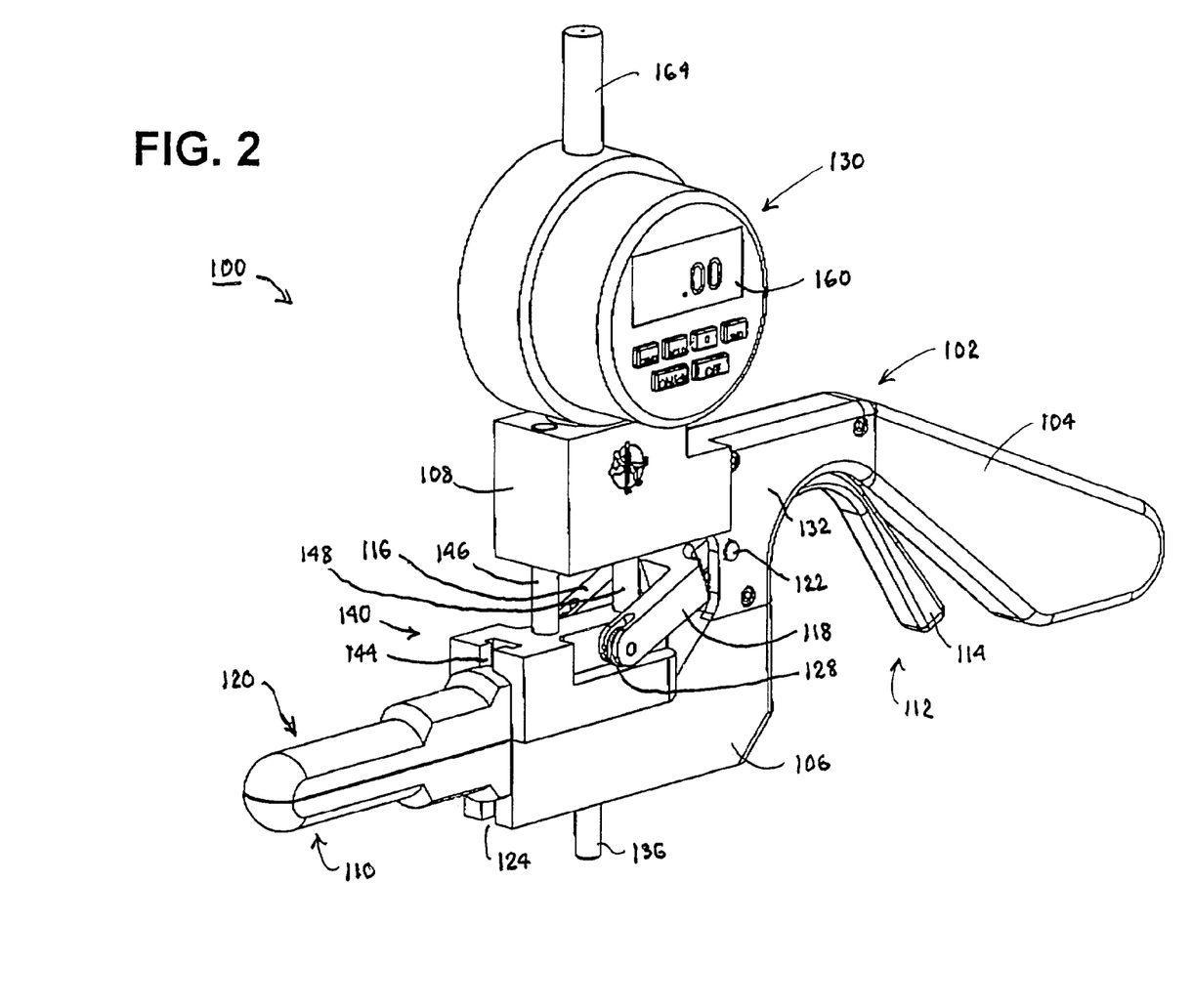
FIG. 2 is a perspective view of the valve lumen sizer of FIG. 1 with the fixed and movable probes maintained in the starting position by holding the trigger against the handle grip in accordance with a first embodiment of the invention.
Figure 3:
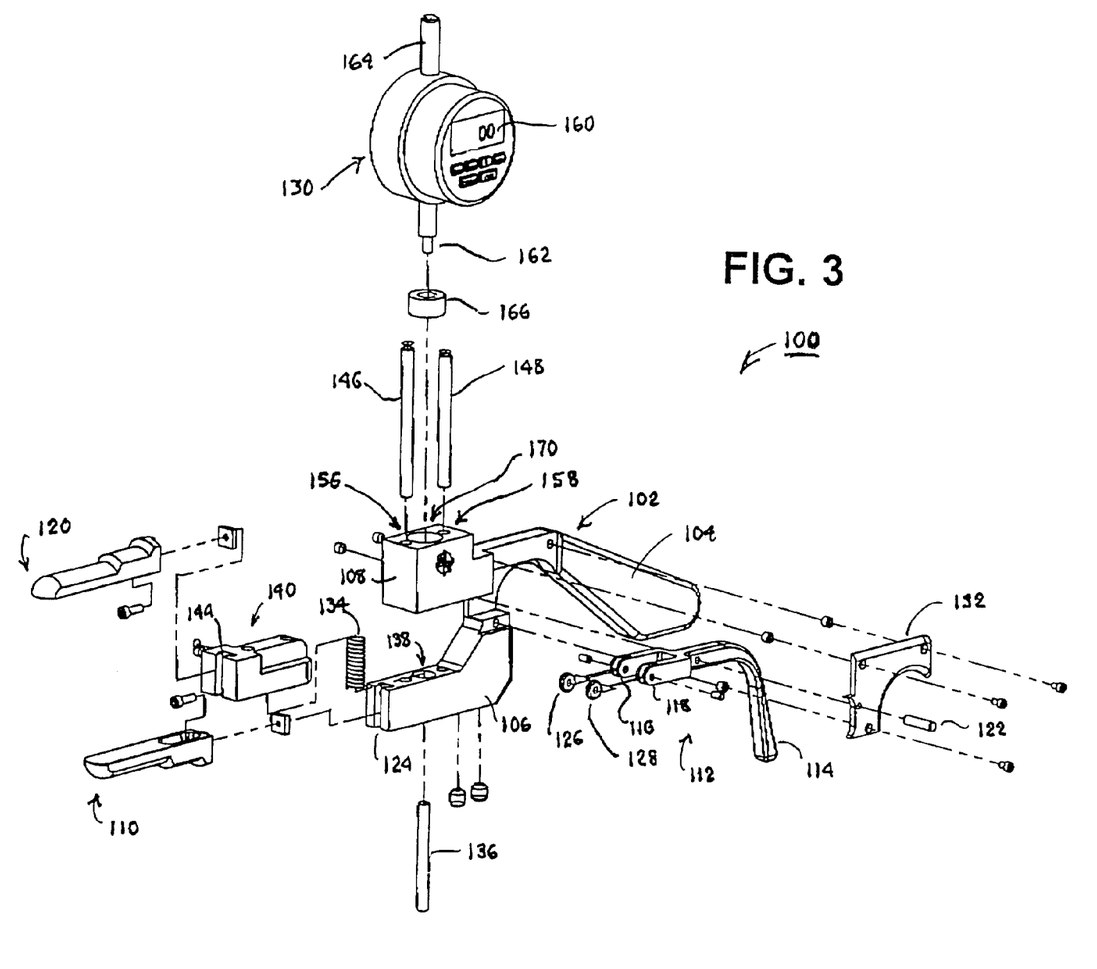
FIG. 3 is an exploded perspective view of the valve lumen sizer of FIGS. 1 and 2.

A first preferred embodiment of a valve annulus sizer 100 for sizing fresh tissue valve isolations is depicted in FIGS. 1-3. A handle assembly 102 supports a stationary probe 110, and a trigger assembly 112 supports a movable probe 120. The movable probe 120 is brought into proximity with the fixed probe 110 when the trigger assembly 112 is brought toward the handle assembly 102 in the starting position depicted in FIG. 2. The movable probe 120 moves away from the fixed probe 110 when the trigger assembly 112 is released as shown in FIG. 1. In use, the movement distance from the starting position of FIG. 2 to the measuring position of FIG. 1 is dictated by and directly proportional to the diameter of the tissue valve lumen of a tissue valve annulus that the fixed and movable probes 110 and 120 are inserted into to make the measurement. The movement distance is measured and displayed at the same time by the gage 130.

More particularly, the handle assembly 102 comprises a handle grip 104 shaped like a pistol grip fitting the user's palm, a lower jaw 106 supporting the stationary probe 110, and a gage platform 108. The flat lower surface of the lower jaw 106 enables the user to set the sizing tool 100 onto a working surface when in the measuring or standby position of FIG. 1.

The trigger assembly 112 comprises the trigger 114 and a lever comprising roller arms 116 and 118 supporting rollers 126 and 128, respectively. The trigger assembly 112 is pivotally mounted to the handle assembly 102 by a trigger pivot intermediate the trigger 114 comprising pivot pin 122 shown in FIG. 3 extending through aligned holes in the handle assembly 102, the trigger assembly 112 and a cover plate 132.

Preferably, the fixed and movable probes 110 and 120 can be removed from the sizing tool 100 and replaced by a replacement probe. In this embodiment, the fixed probe 110 is affixed in a groove 124 at the forward end of the fixed jaw 106 by a nut and bolt as shown in FIG. 3, or an equivalent mechanism, so that the fixed probe 110 can be removed from the fixed jaw 106 and replaced if worn or damaged or replaced by a fixed probe of a different size. The movable probe 120 is similarly affixed in a groove 144 at the forward end of a movable carriage or jaw 140 by a nut and bolt as shown in FIG. 3, or an equivalent mechanism, so that the movable probe 120 can be removed from the movable jaw 140 and replaced if worn or damaged or replaced by a fixed probe of a different size.

The movable jaw 140 is trapped between an upper surface of the fixed jaw 106 and the gage platform 108 by guide pins 146 and 148 extending through respective guide bores 156 and 158 that extend through the gage platform 108, the movable jaw 140, and the fixed jaw 106. The portions of the guide bores 156 and 158 extending through the movable jaw 140 have larger diameters than the diameters of the respective guide pins 146 and 148. The guide pins 146 and 148 are fixed to the gage platform 108 by setscrews threaded through bores of the gage platform 108 into contact with the guide pins 146 and 148. Therefore, the movable jaw 140 and movable probe 120 can be moved back and forth between the starting position of FIG. 2 and the measuring position of FIG. 1 along the guide pins 146 and 148.

The movable jaw 140 is spring biased to move toward the gage platform 108 by a coil spring 134 that is trapped in bore 138 of lower jaw 106. The bore 138 has an upper, large diameter to accommodate the diameter of the coil spring 134 and a lower, small diameter through which a spring guide pin 136 extends. The spring guide pin 136 extends through the bore 138, the lumen of the coil spring 134, and into a bore through the lower surface of the movable jaw 140. The upper end of the spring guide pin 136 is fixed to the fixed jaw 106 by a setscrew threaded through a bore of the fixed jaw 106 into contact with the spring guide pin 136. Thus, the lower end of the spring guide pin 136 can project downward from the fixed jaw 106 when the movable jaw 140 and movable probe 120 are moved into the starting position as shown in FIG. 1. The lower end of the spring guide pin 106 is threaded to accept an adapter for a force gage that can be used to test the force of the coil spring 134. The two threaded holes on the flat lower surface of the lower jaw 106 are used to mount a holding bracket for the force gage.

The gage 130 is of the dial indicator type having a numeric display 160, e.g. an LCD display, that displays the distance that an internally spring loaded gage spindle 162 moves from the starting position of the probes 110 and 120 of FIG. 2 to a measuring position of FIG. 1 upon release of the trigger 114. The spring loaded gage spindle 162 has a lower end that is supported to bear against an upper surface of the movable jaw 140. The gage spindle 162 of the gage 130 is fitted through the lumen of an annular bushing 166 fitted into the further bore 170 into the upper surface of the gage platform 108 so that the drive pin lower end bears against an upper surface of the movable jaw 140. The upper end of the gage spindle 162 extends into the tubular upper extension 164 of the housing of the gage 130.

The rollers 126 and 128 at the ends of the roller arms 116 and 118, respectively, bear against upper surfaces of the movable jaw 140. In the released or measuring position of FIG. 1, the spring force of coil spring 134 forces the movable jaw 140 and the rollers 126 and 128 toward the gage platform 108 and pivots the trigger 114 about the pivot pin 122 away from the handle grip 104. The upward movement of the movable jaw 140 moves the gage spindle 162 upward into the gage 130 and moves the trigger 114 away from the handle grip 104 as the trigger assembly 102 pivots on the pivot pin 122. The linear movement of the gage spindle 162 is measured by a sensor and electronic circuitry within the gage 30, and the distance is displayed in numeric display 160. The reading of the gage 130 appearing in display 160 can be reset to "00" by depressing an ON/CLEAR button provided on the gage 30 near the display 160 when the movable probe 120 is brought to the starting position as shown in FIG. 2. The gage 130 can take the form of the BG4110-3-00002 dial indicator sold by Chicago Dial Indicator Co., DesPlaines, Ill. that reads out distance at a resolution of about 0.01 mm in display 160.

Figure 4:
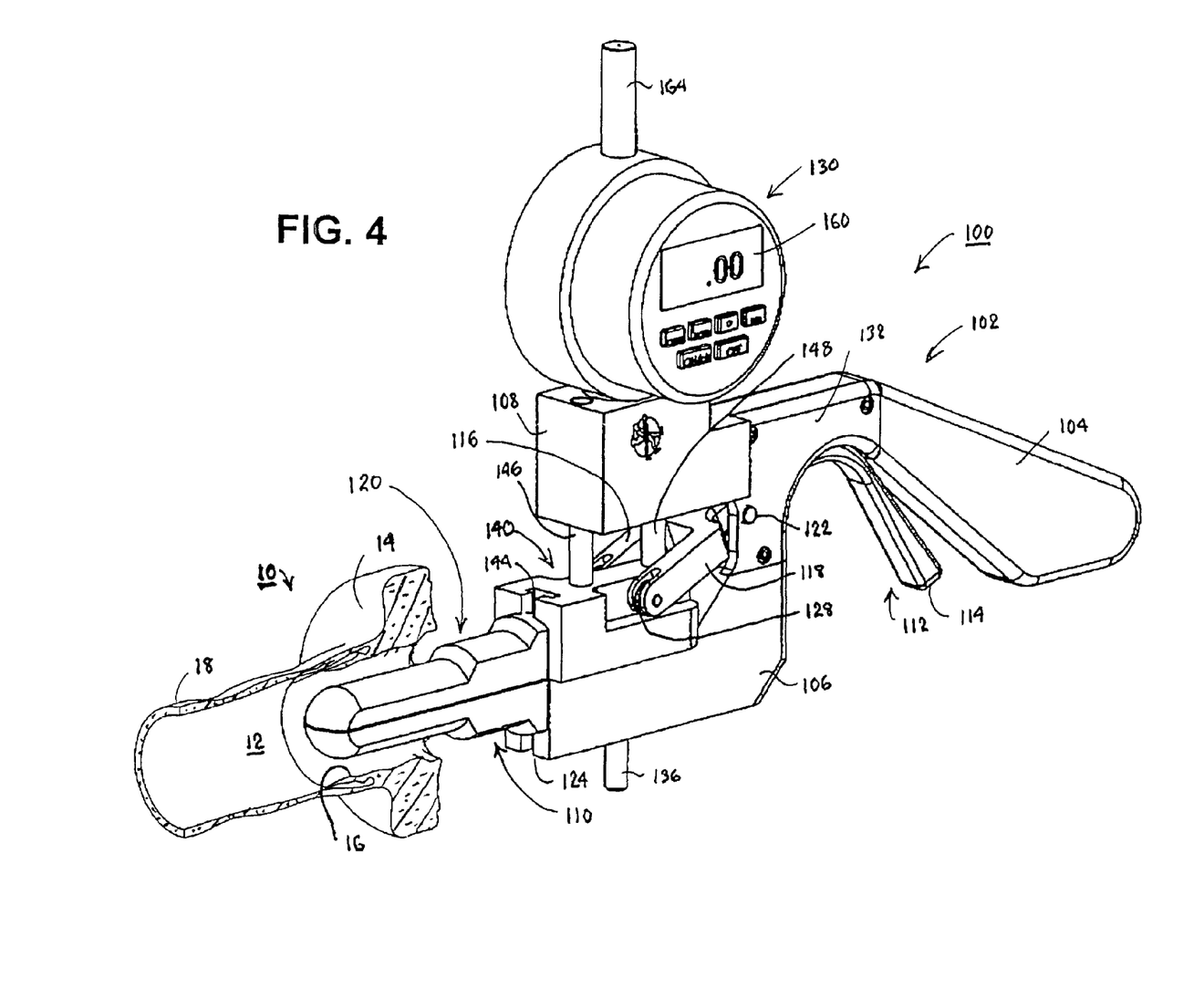
FIG. 4 is a perspective view of the tissue valve isolation depicting, in cross-section, the fixed and movable probes of the valve lumen sizer of FIGS. 1-3 in the starting position within the tissue valve lumen to enable measurement of the valve lumen diameter.
Figure 5:
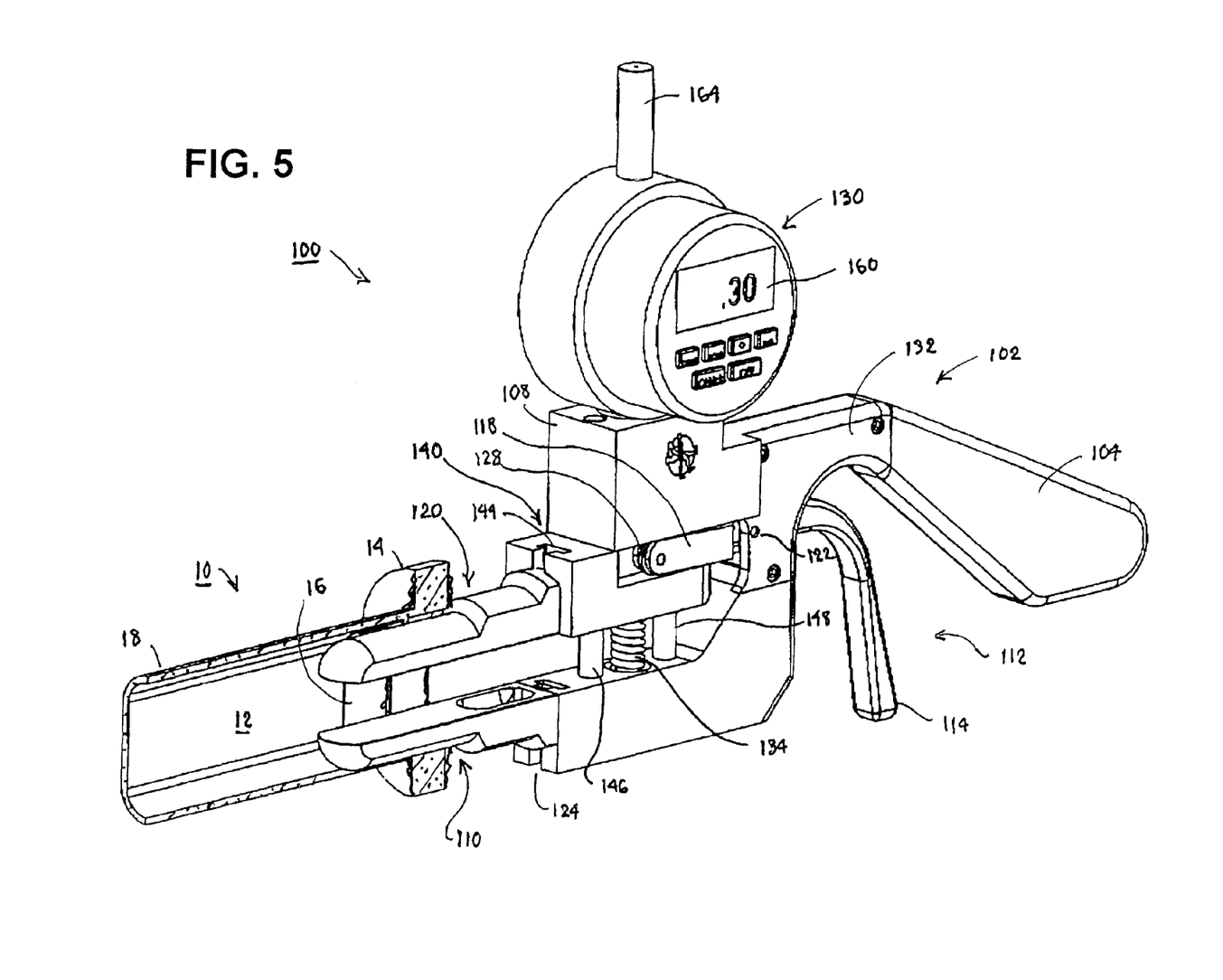
FIG. 5 is a perspective view of the tissue valve isolation depicting, in cross-section, the fixed and movable probes of the valve lumen sizer of FIGS. 1-3 in the measuring position within the tissue valve lumen to measure the valve lumen diameter.

The use of the valve lumen sizer 100 to size a valve lumen 12 of a fresh donor tissue valve isolation 10 is shown in FIGS. 4 and 5. Tissue valve isolation 10 shown in cross-section in FIGS. 4 and 5 comprises the valve annulus 14, the valve leaflets 16 adapted to be extended into the valve lumen 12 when closed and a length of artery 18 attached to the valve annulus 14. The measurement of the diameter of the valve lumen is often characterized as the measurement of the valve annulus.

In accordance with the present invention, the fixed and movable probes 110 and 120 are brought together into the starting position, inserted into the valve lumen 12 as shown in FIG. 4, and the trigger 114 is released to measure the tissue valve annulus 14 as shown in FIG. 5. The user grips the handle grip 104 in the palm of either the right or left hand and presses the fingers against the trigger 114 of the trigger mechanism 112 to squeeze it toward the handle grip 104. The movable probe 120 is then drawn toward the stationary probe 110 against the biasing force of the coil spring 134 to the starting position of FIG. 4 so that the probes 110 and 120 can be inserted into the valve lumen 12 of the tissue valve isolation 10.

The trigger 114 is then released so that the movable probe 120 is moved away from the stationary probe 110 by the biasing coil spring 134. The movement of the probes 110 and 120 elongates the fresh tissue valve lumen 12 and annulus 14 until the resistance presented by the valve annulus 14 equals the biasing force of the biasing spring 134. The movement or separation apart of the probes 110 and 120 is displayed on display 160. The user notes the displayed separation, pulls the trigger 114 back toward the handle 108 to release the tissue valve isolation 10 from the probes 110 and 120, and places the tissue valve isolation 10 into a bin or container for tissue valve isolations of comparable measured sizes. In practice, tissue valve annulus size ranges are defined, and the tissue valve isolations are placed in the bin or container for the size range that the measured valve annulus falls into.

The separation distance between the probes 110 and 120 that is displayed in display 160 is proportional to the actual diameter of the valve lumen 12. The relationship between the separation and the lumen diameter depends in part on the type of tissue valve isolations that are being measured and the shape and size dimensions of the convex opposed surfaces of the probes 110 and 120. As noted below, the fixed and movable probes 110 and 120 may be provided in two or more sizes to be used with particular types of tissue valve isolations. The correlations between displayed distances and true tissue valve diameter for each size of fixed and movable probes 110 and 120 are established empirically.

Figure 6:
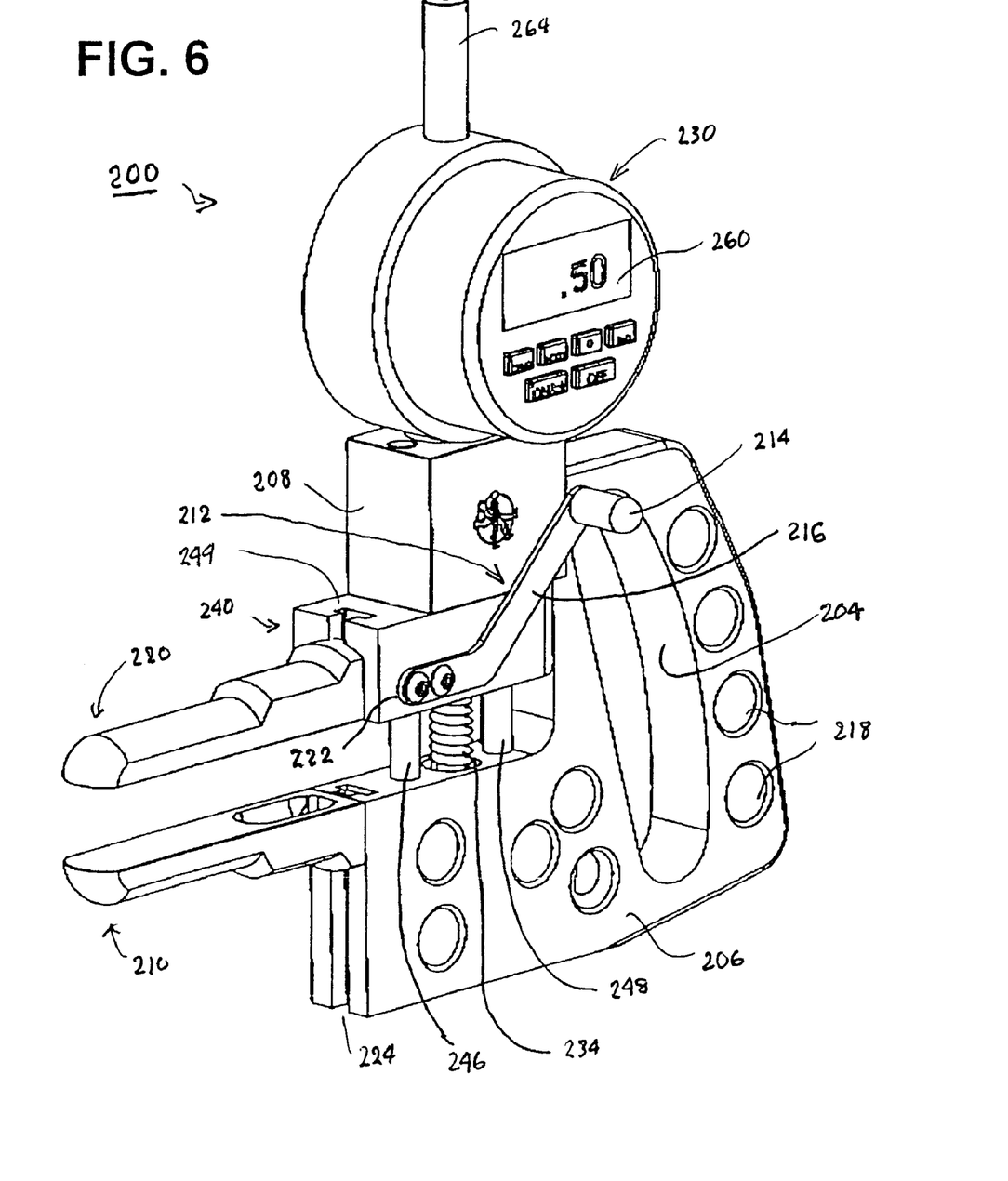
FIG. 6 is a perspective view of a second embodiment of the valve lumen sizer of the present invention with the fixed and movable probes maintained in the measuring position upon release of a crank accordance with a second embodiment of the invention.
Figure 7:
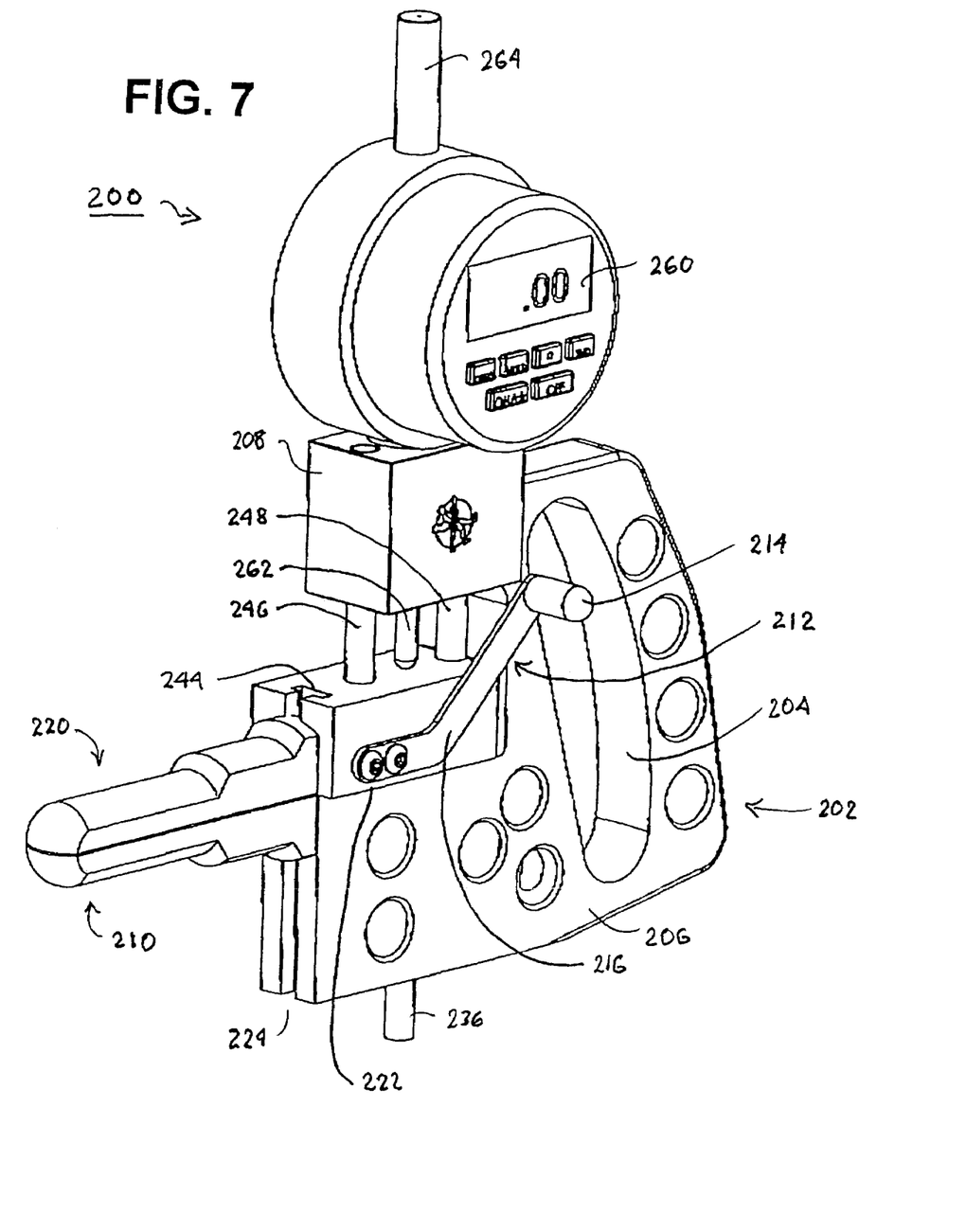
FIG. 7 is a perspective view of the valve lumen sizer of FIG. 6 with the fixed and movable probes in a starting position by holding the crank down in accordance with the second embodiment of the invention.
Figure 8:
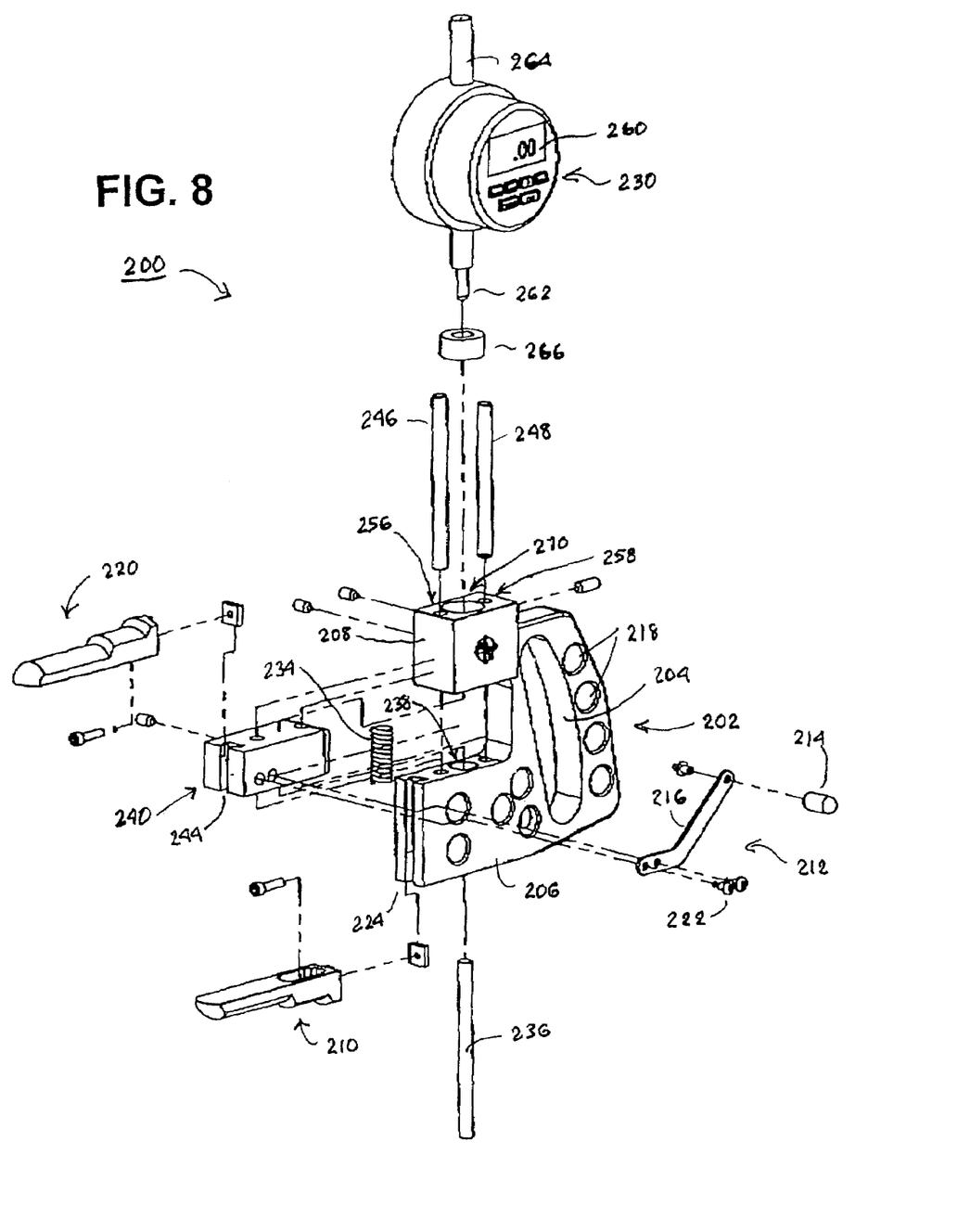
FIG. 8 is an exploded perspective view of the valve lumen sizer of FIGS. 6 and 7.

A second preferred embodiment of a valve annulus sizer 200 for sizing fresh tissue valve isolations is depicted in FIGS. 6-8. A handle assembly 202 supports a stationary probe 210, and a crank assembly 212 supports a movable probe 220. The movable probe 220 is brought into proximity with the fixed probe 210 when the crank assembly 212 is depressed downward alongside the handle assembly 202 to move the movable probe 220 to the starting position depicted in FIG. 7. The movable probe 220 moves away from the fixed probe 210 when the crank assembly 212 is released as shown in FIG. 6. In use, the movement distance from the starting position of FIG. 7 to the measuring position of FIG. 6 is dictated by and directly proportional to the diameter of the tissue valve lumen of a tissue valve annulus that the fixed and movable probes 210 and 220 are inserted into to make the measurement. The movement distance is measured and displayed at the same time by the gage 230.

More particularly, the handle assembly 202 is formed having a handle grip 204 that is grasped by the user's fingers and palm. The handle assembly 202 extends forward from the handle grip 204 through a lower jaw 206 supporting the stationary probe 210 and an upper gage platform 208. A number of through-holes, e.g., hole 203, are formed through the handle assembly to lower the overall weight of the sizer 200. The flat lower surface of the fixed lower jaw 206 enables the user to set the sizing tool 200 onto a working surface when in the measuring or standby position of FIG. 6.

Figure 9:
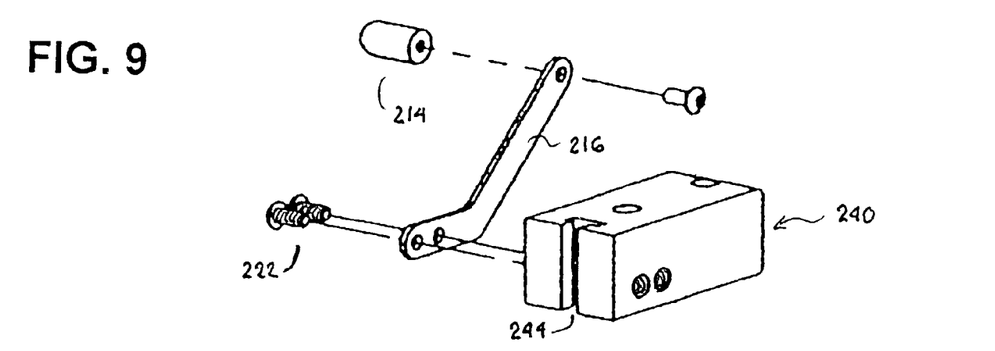
FIG. 9 is a perspective view of the movable jaw that the crank can be attached to for right or left hand use of the valve lumen sizer of the second embodiment of the invention depicted in FIGS. 6-8.

The crank assembly 212 comprises a crank arm 216 extending from a side of the movable jaw 240 to a thumb knob 214 that is engaged by the user's thumb when the user grips the handle grip 204 to move a movable jaw 240 downward to thereby move the movable probe 220 from the standby or measuring position of FIG. 6 to the starting position of FIG. 7. As shown in FIGS. 6-8, the crank arm 216 is mounted to one side of the movable jaw 240 by bolts 222 to accommodate users who grasp the sizer 200 with the right hand. As shown in FIG. 9, the crank arm 216 can be mounted to the other side of the movable jaw 240 by bolts 222 to accommodate users who grasp the sizer 200 with the left hand. The user or operator applies his or her right or left thumb to the crank knob 214 to move the crank assembly 212, movable jaw 240, and movable probe 220 downward to bring the movable and fixed probes 220 and 210 together.

Preferably, the fixed and movable probes 210 and 220 can be removed from the sizing tool 200 and replaced by a replacement probe. In this embodiment, the fixed probe 210 is affixed in a groove 224 at the forward end of the fixed jaw 206 by a nut and bolt as shown in FIG. 8, or an equivalent mechanism, so that the fixed probe 210 can be removed from the fixed jaw 206 and replaced if worn or damaged or replaced by a fixed probe of a different size. The movable probe 220 is similarly affixed in a groove 244 at the forward end of a movable carriage or jaw 240 by a nut and bolt as shown in FIG. 8, or an equivalent mechanism, so that the movable probe 220 can be removed from the movable jaw 240 and replaced if worn or damaged or replaced by a fixed probe of a different size.

The movable jaw 240 is trapped between the upper surface of the fixed jaw 206 and the lower surface of the gage platform 208 by guide pins 246 and 248 extending through respective guide bores 256 and 258 that extend through the gage platform 208, the movable jaw 240, and the fixed jaw 206. The portions of the guide bores 256 and 258 extending through the movable jaw 240 have larger diameters than the diameters of the respective guide pins 246 and 248. The guide pins 246 and 248 are fixed to the gage platform 208 by setscrews threaded through bores of the gage platform 208 into contact with the guide pins 246 and 248. Therefore, the movable jaw 240 and movable probe 220 can be moved back and forth between the starting position of FIG. 7 and the measuring position of FIG. 6 along the guide pins 246 and 248.

The movable jaw 240 is spring biased to move toward the gage platform 208 by a coil spring 234 that is trapped in bore 238 of lower jaw 206. The bore 238 has an upper, large diameter to accommodate the diameter of the coil spring 234 and a lower, small diameter through which a spring guide pin 236 extends. The spring guide pin 236 extends through the bore 238, the lumen of the coil spring 234, and into a bore through the lower surface of the movable jaw 240. The upper end of the spring guide pin 236 is fixed to the fixed jaw 206 by a setscrew threaded through the fixed jaw 206 into contact with spring guide pin 236. Thus, the lower end of the spring guide pin 236 can project downward from the fixed jaw 206 when the movable jaw 240 and movable probe 220 are moved into the starting position as shown in FIG. 7. The lower end of the spring guide pin 206 is threaded to accept an adapter for a force gage that can be used to test the force of the coil spring 234. The two threaded holes on the flat lower surface of the lower jaw 206 are used to mount a holding bracket for the force gage.

The gage 230 has a numeric display 260, e.g. an LCD display, that displays the distance that an internally spring loaded gage spindle 262 moves from the starting position of the probes 210 and 220 of FIG. 7 to a measuring position of FIG. 6 upon release of the trigger 214. The spring loaded gage spindle 262 has a lower end that is supported to bear against an upper surface of the movable jaw 240. The gage spindle 262 of the gage 230 is fitted through the lumen of an annular 266 fitted into the further bore 270 into the upper surface of the gage platform 208 so that the drive pin lower end bears against an upper surface of the movable jaw 240. The upper end of the gage spindle 262 extends into the tubular upper extension 264 of the housing of the gage 230.

In the standby or measuring position of FIG. 6, the spring force of coil spring 234 forces the movable jaw 240 toward the gage platform 208. The upward movement of the movable jaw 240 moves the gage spindle 262 upward into the gage 230 and moves the crank assembly 214 upward. The linear movement of the spring loaded gage spindle 262 is measured by a sensor and electronic circuitry within the gage 30, and the distance is displayed in numeric display 260. The reading of the gage 230 appearing in display 260 can be reset to "00" by depressing a zeroing button provided on the gage 30 near the display 260 when the movable probe 220 is brought to the starting position as shown in FIG. 7. The gage 230 can take the form as the above-described gage 130.

The use of the valve lumen sizer 200 to size a valve lumen 12 of a fresh donor tissue valve isolation 10 shown in FIGS. 4 and 5 is much the same as that described above in reference to FIGS. 4 and 5. The fixed and movable probes 210 and 220 are brought together into the starting position of FIG. 7 as described above and inserted into the valve lumen 12 in the same manner as shown in FIG. 4. The user slowly releases pressure against the thumb knob 214 so that the movable probe 220 moves away from the stationary fixed probe 210 to measure the tissue valve annulus 14 in the same manner as shown in FIG. 5.

The movement of the probes 210 and 220 elongates the fresh tissue valve lumen 12 and annulus 14 in the manner shown in FIG. 5 until the resistance presented by the valve annulus 14 equals the biasing force of the biasing spring 234. The movement or separation apart of the probes 210 and 220 is displayed on display 260. The user notes the displayed separation, and then depresses the crank handle 214 back downward toward the lower jaw 206 to release the tissue valve isolation 10 from the probes 210 and 220, and places the tissue valve isolation 10 into a bin or container for tissue valve isolations of comparable measured sizes as described above.

Again, the separation distance between the probes 210 and 120 that is displayed in display 260 is proportional to the actual diameter of the valve lumen 12. The relationship between the separation and the lumen diameter depends in part on the type of tissue valve isolations that are being measured and the shape and size dimensions of the convex opposed surfaces of the probes 210 and 220. As noted below, the fixed and movable probes 210 and 220 may be provided in two or more sizes to be used with particular types of tissue valve isolations. The correlations between displayed distances and true tissue valve diameter for each size of fixed and movable probes 210 and 220 are established empirically.

The spring tension of the coils 134 and 234 is set fairly low, on the order of less than five pounds per inch of compression. The maximum separation of the movable jaws from the fixed jaws is less than one inch, and so the maximum force applied to the annulus tissue of fresh tissue valve isolations during measurement is less than five pounds. Consequently, the spring force on the tissue annulus is relatively low and not injurious to the tissue, even if the trigger 114 or crank knob 214 is released rapidly by the user. The resulting readings of the separation distance of the probes are highly repeatable and accurate.

Figure 10A:
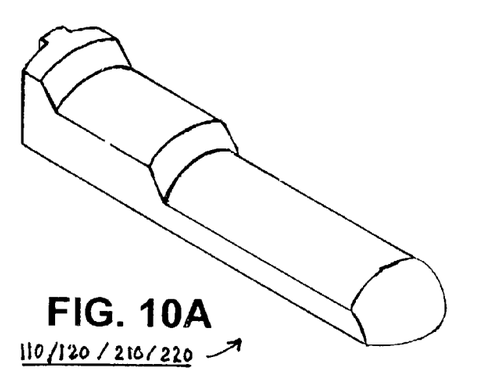
FIG. 10A is a perspective view of the movable and stationary probes having a large width and tissue contacting surface radius for use in the sizers of the present invention to size tissue valves having a relatively large valve lumen diameter.
Figure 10B:
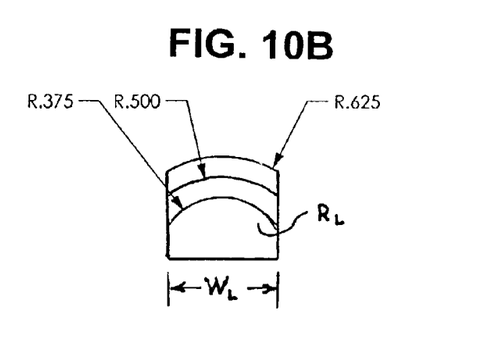
FIG. 10B is an end view of the probe of FIG. 10A illustrating the large probe width and tissue contacting surface radius.
Figures 11A, 11B:
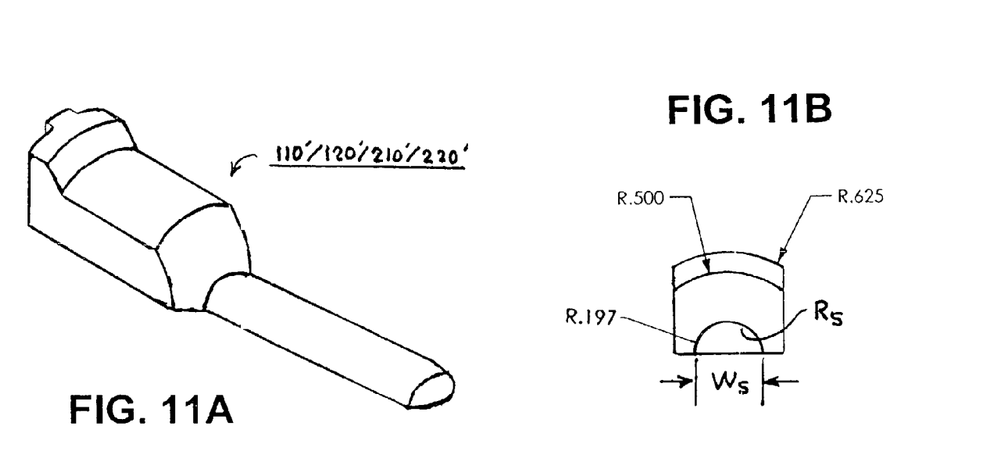
FIG. 11A is a perspective view of a movable and stationary probe having a small width and tissue contacting surface radius for use in the sizers of the present invention to size tissue valves having a relatively small valve lumen diameter.
FIG. 11B is an end view of the probe of FIG. 11A illustrating the small probe width and tissue contacting surface radius.

As noted above, the fixed and movable probes 110/120/ 210/220 can be removed from the fixed and movable jaws and replaced when damaged or to size differing ranges of tissue valves. FIGS. 10A and 10B depict the movable and stationary probes 110/120/210/220 having a first width and tissue contacting surface radius for use in the sizers 100 and 200 to size tissue valves having a relatively large valve lumen diameter. FIG. 10B shows an exemplary large radius $R_L$ of the tissue-contacting surface extending across the probe width $W_L$. FIGS. 11A and 11B depict the movable and stationary probes 110'/120'/210'/220' having a narrow width and small tissue contacting surface radius for use in the sizers 100 and 200 to size tissue valves having a relatively small valve lumen diameter. FIG. 11B shows an exemplary small radius $R_S$ of the tissue contacting surface extending across the narrow probe width $W_S$.

The small probes 110'/120'/210'/220' were developed so that tissue valve isolations would not be damaged by such probes that are close to, if not, the same size as the small diameter tissue valve lumens. Using the valve lumen sizers of the present invention with large and small probes of FIGS. 10A, 10B and 11A, 11B provides actual measurements that are approximately the same for large and small tissue valve lumens, respectively. The user or operator obtains the direct valve lumen size reading directly from the gauge reading and can sort the tissue valve isolation into a size category based on ranges that are empirically derived.

These ranges were determined in a study comparing the gage readings of fresh tissue valve lumens were compared to fixed tissue valve lumens. The tissue valve lumens of relatively large fresh donor tissue valve isolations were measured by use of a valve lumen sizer of the present invention with the large probes, and the measurements were retained. Similarly, the tissue valve lumens of relatively small fresh donor tissue valve isolations were measured by use of a valve lumen sizer of the present invention with the small probes, and the measurements were retained. The measured fresh tissue valve isolations were processed through trimming and fixation to be ready to be assembled into prosthetic tissue valves. The fixed valve lumens were then measured, and fixed valve lumen size measurements were correlated to the retained corresponding fresh valve lumen size gage readings. The fixed valve lumen size ranges or tolerances for each prosthetic tissue valve are determined, and the corresponding fresh tissue valve lumen size readings are thereby determined for the probe size that was used in fresh tissue valve lumen size reading. The gage reading ranges (for each probe size) correlated to the fixed tissue valve size ranges were further refined for individual suppliers by following tissue from the suppliers through the fixation process and adjusting the initially determined fresh tissue valve lumen gage reading ranges upwards or downwards depending upon the size of the tissue valve lumen after fixation.

Thus, it will be appreciated that the methods and sizers of the present invention advantageously increase the accuracy and speed of sizing fresh donor tissue heart valve isolations and can lead to lower manufacturing costs in making tissue valve prostheses from the sized tissue valves.

All patents and publications referenced herein are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments. The disclosed embodiments are presented for purposes of illustration and not limitation, and the present invention is limited only by the claims that follow.

The invention claimed is:

1. A sizing tool for sizing the tissue valve lumen of a tissue valve annulus of a fresh donor tissue valve isolation by a user comprising:
   means adapted to be grasped in a user's hand for supporting first and second probes;
   wherein the means for supporting the first and second probes further comprises a handle mechanism having a handle grip adapted to be grasped by the user and a movable jaw supporting the second probe extending away from the movable jaw, respectively, the handle mechanism further comprising a fixed jaw supporting the first probe extending away from the fixed jaw, wherein:
   the handle mechanism comprises a gage platform;
   the movable jaw is supported by jaw guides between the gage platform and the fixed jaw;
   means operable by the user for moving the second probe toward the first probe while the first probe remains stationary in disposing the first and second probes in a starting position enabling insertion of the first and second probes into the tissue valve lumen;
   wherein the means for disposing the first and second probes in a starting position comprises a trigger mechanism having a trigger adapted to be pulled by the user grasping the handle grip to urge the movable jaw toward the fixed jaw thereby disposing the first and second probes in a starting position;
   means for linearly separating the first and second probes apart within the tissue valve lumen until the first and second probes are restrained from further movement by contact with the tissue valve annulus;
   wherein the means for separating the first and second probes apart comprises a bias spring disposed between the fixed jaw and the movable jaw that urges the movable jaw away from the fixed jaw to separate the first probe from the second probe; and
   means for measuring the separation distance that the first and second probes are moved apart, whereby the measurement provides an indication of the tissue valve lumen diameter.

2. The sizing tool of claim 1, wherein means for supporting comprises means for supporting first and second probes selected from small lumen measuring probes and large lumen measuring probes, respectively, to measure small diameter tissue valve lumens or large diameter tissue valve lumens, respectively.

3. The sizing tool of claim 1, wherein the trigger mechanism comprises a lever arm extending from the trigger and a pivot intermediate the lever arm and the trigger attaching the trigger mechanism to the handle and disposing the lever arm against the movable jaw, whereby the lever arm urges the movable jaw toward the fixed jaw along the jaw guides thereby disposing the first and second probes in the starting position as the trigger is pulled toward the handle grip.

4. The sizing tool of claim 3, wherein the measuring means comprises a distance measuring gage supported by the handle mechanism and in contact with the movable jaw that displays a measurement of the separation distance that the second probe is from the first probe as the trigger is released.

5. The sizing tool of claim 1, wherein the trigger mechanism comprises a lever arm extending from the trigger and a pivot intermediate the lever arm and the trigger attaching the trigger mechanism to the handle and disposing the lever arm against the movable jaw, whereby the lever arm urges the movable jaw toward the fixed jaw thereby disposing the first and second probes in the starting position as the trigger is pulled toward the handle grip.

6. The sizing tool of claim 5, wherein the measuring means comprises a distance measuring gage supported by the handle mechanism and in contact with the movable jaw that displays a measurement of the separation distance that the second probe is from the first probe as the trigger is released.

7. The sizing tool of claim 1, wherein the measuring means comprises a distance measuring gage supported by the handle mechanism and in contact with the movable jaw that displays a measurement of the separation distance that the second probe is from the first probe as the trigger is released.

8. The sizing tool of claim 1, wherein:
the fixed jaw comprises a first attachment mechanism for attachment of the first probe to the fixed jaw and for release of the first probe from the fixed jaw;
the movable jaw comprises a second attachment mechanism for attachment of the second probe to the movable jaw and for release of the second probe from the movable jaw,
whereby the first and second probes can be selected from small lumen measuring probes and large lumen measuring probes and attached to the fixed and movable jaws, respectively, to measure small diameter tissue valve lumens or large diameter tissue valve lumens, respectively.

9. A sizing tool for sizing the tissue valve lumen of a tissue valve annulus of a fresh donor tissue valve isolation by a user comprising;
a handle mechanism having a handle grip adapted to be grasped by the user, a gage platform, and a fixed jaw supporting a fixed probe extending away from the fixed jaw;
a movable jaw supporting a movable probe extending away from the movable jaw;
a jaw guide supporting the movable jaw for movement between the fixed jaw and the gage platform;
a bias spring disposed between the fixed jaw and the movable jaw that urges the movable jaw away from the fixed jaw to separate the first probe from the second probe until the fixed and movable probes are restrained from further movement by contact with the tissue valve annulus;
a trigger mechanism having a trigger adapted to be pulled by the user grasping the handle grip and a lever arm in contact with the moveable jaw and extending between the moveable jaw and the gage platform to urge the movable jaw against the bias spring toward the fixed jaw, thereby disposing the fixed and movable probes in a starting position enabling insertion of the fixed and movable probes into the tissue valve lumen; and
a distance measuring gage supported by the gage platform having a gage spindle in operative contact with the movable jaw that measures the separation distance that the movable probe moves away from the fixed probe, whereby the measurement provides an indication the tissue valve lumen diameter.

10. The sizing tool of claim 9, wherein the trigger mechanism comprises a pivot intermediate the lever arm and the trigger attaching the trigger mechanism to the handle and disposing the lever arm against the movable jaw, whereby the lever arm urges the movable jaw toward the fixed jaw along the jaw guide thereby disposing the fixed and movable probes in the starting position as the trigger is pulled toward the handle grip.

11. The sizing tool of claim 10, wherein the distance-measuring gage provides a measurement of the separation distance that the second probe is from the first probe as the trigger is released by the user.

12. The sizing tool of claim 10, wherein:
the fixed jaw comprises a first attachment mechanism for attachment of the fixed probe to the fixed jaw and for release of the fixed probe from the fixed jaw;
the movable jaw comprises a second attachment mechanism for attachment of the movable probe to the movable jaw and for release of the movable probe from the movable jaw,
whereby the fixed and movable probes can be selected from small lumen measuring probes and large lumen measuring probes and attached to the fixed and movable jaws, respectively, to measure small diameter tissue valve lumens or large diameter tissue valve lumens, respectively.

13. The sizing tool of claim 9, wherein:
the fixed jaw comprises a first attachment mechanism for attachment of the fixed probe to the fixed jaw and for release of the fixed probe from the fixed jaw;
the movable, jaw comprises a second attachment mechanism for attachment of the movable probe to the movable jaw and for release of the movable probe from the movable jaw,
whereby the fixed and movable probes can be selected from small lumen measuring probes and large lumen measuring probes and attached to the fixed and movable jaws, respectively, to measure small diameter tissue valve lumens or large diameter tissue valve lumens, respectively.

14. The sizing tool of claim 9, wherein the gage displays the separation distance and the display is resettable to a reference value reading when the trigger is pulled to move the movable probe to the starting position.

15. A sizing tool for sizing the tissue valve lumen of a tissue valve annulus of a fresh donor tissue valve isolation by a user comprising;
a handle mechanism having a handle grip adapted to be grasped by the user, a gage platform, and a fixed jaw supporting a fixed probe extending away from the fixed jaw;
a movable jaw supporting a movable probe extending away from the movable jaw;
a jaw guide supporting the movable jaw for non-pivoting movement between the fixed jaw and the gage platform;
a bias spring disposed between the fixed jaw and the movable jaw that urges the movable jaw away from the fixed jaw to separate the first probe from the second probe until the fixed and movable probes are restrained from further movement by contact with the tissue valve annulus;
a crank mechanism having a crank arm and a crank knob adapted to be engaged by the user grasping the handle grip to urge the movable jaw toward the fixed jaw, thereby disposing the fixed and movable probes in a starting position enabling insertion of the fixed and movable probes into the tissue valve lumen, the crank arm being non-pivotably attached to the moveable jaw; and
a distance measuring gage supported by the gage platform having a gage spindle in operative contact with the movable jaw that measures the separation distance that the movable probe moves away from the fixed probe, whereby the measurement provides an indication the tissue valve lumen diameter.

16. The sizing tool of claim 15, wherein the distance measuring gage provides a measurement of the separation distance that the second probe is from the first probe as the crank knob is released by the user.

17. The sizing tool of claim 15, wherein depression of the crank knob urges the movable jaw toward the fixed jaw along the jaw guide thereby disposing the fixed and movable probes in the starting position.

18. The sizing tool of claim 17, wherein:
the fixed jaw comprises a first attachment mechanism for attachment of the fixed probe to the fixed jaw and for release of the fixed probe from the fixed jaw;
the movable jaw comprises a second attachment mechanism for attachment of the movable probe to the movable jaw and for release of the movable probe from the movable jaw,
whereby the fixed and movable probes can be selected from small lumen measuring probes and large lumen measuring probes and attached to the fixed and movable jaws, respectively, to measure small diameter tissue valve lumens or large diameter tissue valve lumens, respectively.

19. The sizing tool of claim 15, wherein:
the movable jaw comprises first and second opposite sides; and
the crank mechanism comprises a crank arm extending from the crank knob to a point of attachment with the movable jaw on a selected one of the first and second sides to accommodate the right or left hand of the user, whereby the depression of the crank knob urges the movable jaw toward the fixed jaw along the jaw guides thereby disposing the fixed and movable probes in the starting position.

20. The sizing tool of claim 15, wherein the gage displays the separation distance and the display is resettable to a reference value reading when the crank knob is depressed to move the movable probe to the starting position.

21. A sizing tool for sizing the tissue valve lumen of a tissue valve annulus of a fresh donor tissue valve isolation by a user comprising:
means adapted to be grasped in a user's hand for supporting first and second probes;
wherein the means for supporting the first and second probes comprises a handle mechanism having a handle grip adapted to be grasped by the user and a movable jaw supporting the second probe extending away from the movable jaw, respectively, the handle mechanism further comprising a fixed jaw supporting the first probe extending away from the fixed jaw, wherein: the handle mechanism comprises a gage platform; the movable jaw is supported by jaw guides between the gage platform and the fixed jaw;
means operable by the user for moving the second probe toward the first probe while the first probe remains stationary in disposing the first and second probes in a starting position enabling insertion of the first and second probes into the tissue valve lumen;
wherein the means for disposing the first and second probes in a starting position comprises a crank mechanism having a crank knob adapted to be engaged by the user grasping the handle grip to urge the movable jaw toward the fixed jaw thereby disposing the first and second probes in a starting position;
means for linearly separating the first and second probes apart within the tissue valve lumen until the first and second probes are restrained from further movement by contact with the tissue valve annulus;
wherein the means for separating the first and second probes apart comprises a bias spring disposed between the fixed jaw and the movable jaw that urges the movable jaw away from the fixed jaw to separate the first probe from the second probe; and
means for measuring the separation distance that the first and second probes are moved apart, whereby the measurement provides an indication of the tissue valve lumen diameter.

22. The sizing tool of claim 21, wherein the crank mechanism comprises a crank arm extending from the crank knob to a point of attachment with the movable jaw, whereby the depression of the crank knob urges the movable jaw toward the fixed jaw along the jaw guides thereby disposing the first and second probes in the starting position.

23. The sizing tool of claim 22, wherein the measuring means comprises a distance measuring gage supported by the handle mechanism and in contact with the movable jaw that displays a measurement of the separation distance that the second probe is from the first probe as the crank knob is released.

24. The sizing tool of claim 21, wherein the crank mechanism comprises a crank arm extending from the crank knob to a point of attachment with the movable jaw, whereby the depression of the crank knob urges the movable jaw toward the fixed jaw thereby disposing the first and second probes in the starting position.

25. The sizing tool of claim 24, wherein the measuring means comprises a distance measuring gage supported by the handle mechanism and in contact with the movable jaw that displays a measurement of the separation distance that the second probe is from the first probe as the crank knob is released.

26. The sizing tool of claim 21, wherein the measuring means comprises a distance measuring gage supported by the handle mechanism and in contact with the movable jaw that displays a measurement of the separation distance that the second probe is from the first probe as the crank knob is released.

27. The sizing tool of claim 21, wherein:
the fixed jaw comprises a first attachment mechanism for attachment of the first probe to the fixed jaw and for release of the first probe from the fixed jaw;
the movable jaw comprises a second attachment mechanism for attachment of the second probe to the movable jaw and for release of the second probe from the movable jaw,
whereby the first and second probes can be selected from small lumen measuring probes and large lumen measuring probes and attached to the fixed and movable jaws, respectively, to measure small diameter tissue valve lumens or large diameter tissue valve lumens, respectively.

28. The sizing tool of claim 21, wherein:
the movable jaw comprises first and second opposite sides; and
the crank mechanism comprises a crank arm extending from the crank knob to a point of attachment with the movable jaw on a selected one of the first and second sides to accommodate the right or left hand of the user, whereby the depression of the crank knob urges the movable jaw toward the fixed jaw along the jaw guides thereby disposing the first and second probes in the starting position.

* * * * *